United States Patent [19]

Fay

[11] 3,946,159

[45] Mar. 23, 1976

[54] HOSPITAL COMMUNICATION SYSTEM
[75] Inventor: James P. Fay, Ranchester, Wyo.
[73] Assignee: Vital Signs, Incorporated, Ranchester, Wyo.
[22] Filed: June 20, 1975
[21] Appl. No.: 588,640

Related U.S. Application Data
[63] Continuation of Ser. No. 344,361, March 23, 1973, abandoned.

[52] U.S. Cl. ............ 179/2 TV; 179/37; 179/15 FD; 340/182; 128/2.1 A
[51] Int. Cl.² ....................................... H04M 11/06
[58] Field of Search .................... 179/2 TV, 37–39, 179/1 H, 1 CW, 15 FD, 15 BL, 2 R, 2 A; 340/180, 182, 221, 311; 128/2.1 A, 2.06

[56] References Cited
UNITED STATES PATENTS

| | | | |
|---|---|---|---|
| 2,892,033 | 6/1959 | Corrigan | 179/1 H |
| 2,910,680 | 10/1959 | McLain | 340/311 |
| 3,304,376 | 2/1967 | Truby | 179/1 H |
| 3,426,151 | 2/1969 | Tygart | 179/2 A |
| 3,465,103 | 9/1969 | Lynch | 340/182 |
| 3,572,316 | 3/1971 | Vogelman et al. | 340/182 |
| 3,691,295 | 9/1972 | Fisk | 179/2 TV |
| 3,786,190 | 1/1974 | Pori | 179/15 FD |
| 3,816,662 | 6/1974 | Shaver et al. | 179/2 TV |

FOREIGN PATENTS OR APPLICATIONS

| | | | |
|---|---|---|---|
| 800,176 | 11/1968 | Canada | 179/2 A |

*Primary Examiner*—Kathleen H. Claffy
*Assistant Examiner*—Gerald L. Brigance
*Attorney, Agent, or Firm*—Sheridan, Ross & Fields

[57] ABSTRACT

A communication system that uses a separate single coaxial cable to link a nurse's station to each of a plurality of patient rooms is disclosed. Each cable carries DC message signals from the patient rooms to the nurse's station to alert the nurse on duty that her assistance is needed either on an emergency or on a non-emergency basis. The coaxial cables also carry AC power to power TV receivers located in the patient rooms. In addition, the coaxial cables carry normal video signals to the receiver; audio and visual communication signals between patients and the nurses station; and, telemetry from patient sensors to the nurses station. Further, the system is adapted to automatically allow a patient to view the nurse at the nurses station on the TV receiver located in the patient's room when the patient is communicating with the nurse regardless of whether or not the TV receiver was on or off at the time such communication commences.

14 Claims, 6 Drawing Figures

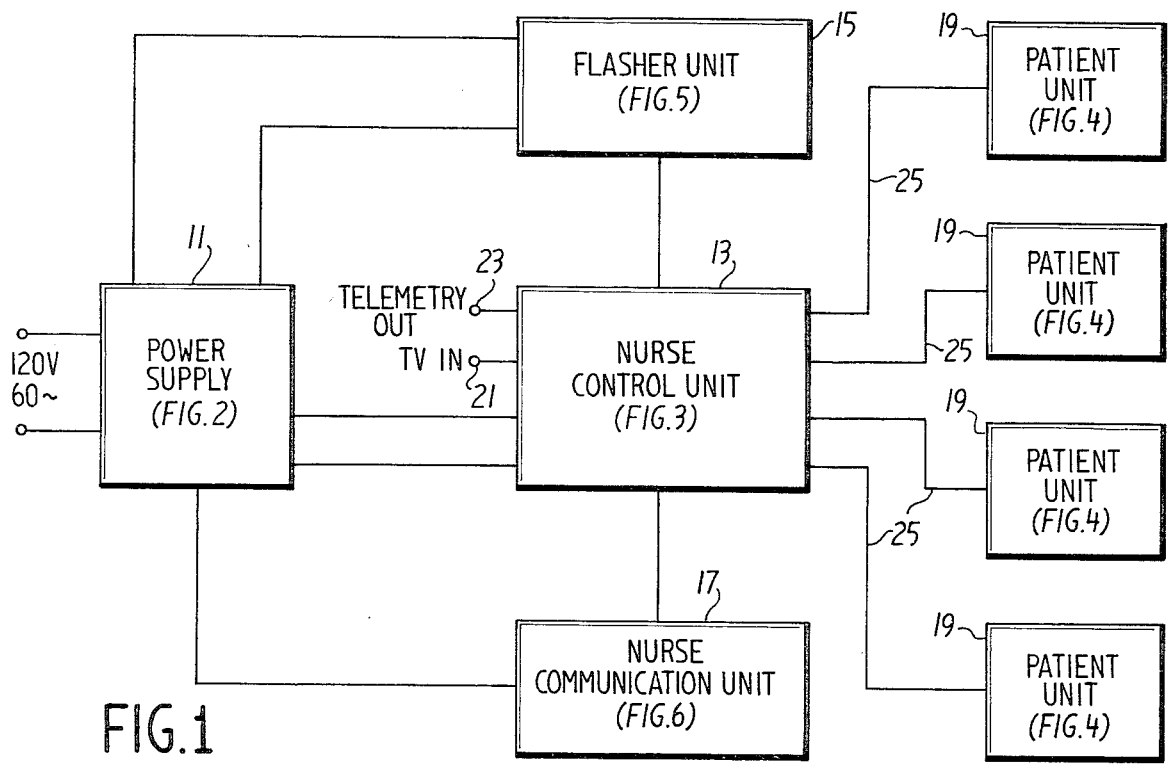
FIG.1
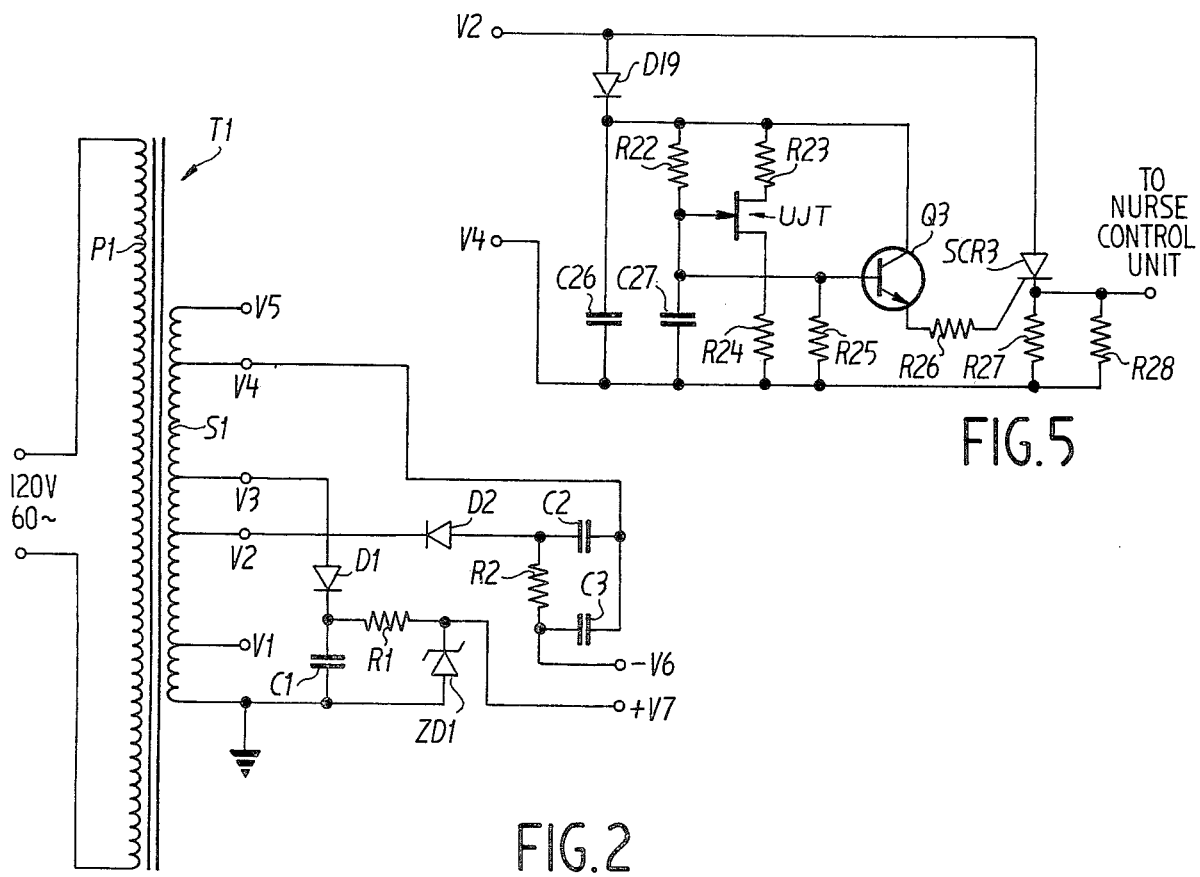
FIG.2
FIG.5

HOSPITAL COMMUNICATION SYSTEM

This is a continuation of application Ser. No. 344,361, filed Mar. 23, 1973, now abandoned.

BACKGROUND OF THE INVENTION

This invention relates to communication systems and more particularly to a communication system for communicating between hospital room patients and a central nurses' station.

Many hospitals, because of communication problems, do not use their personnel (primarily nurses) in the most efficient manner. The present preferred way of best utilizing a nurse's time is for one or more nurses to be stationed at a central nurses station. From this station, the nurse services a floor, a wing, or a plurality of rooms of a hospital, depending upon the size and layout of the hospital, by continuously rotating through the rooms assigned to her to check on "her" patient's condition. This method of operation has several disadvantages. It requires that the nurse be constantly moving and, thus, is physically exhausting. In addition, a nurse may be checking on one patient when an emergency occurs to another patient, and, thus, she may not be alerted in time to assist the patient with the emergency. To alleviate this undesirable situation, most hospitals have installed what is commonly known as a "nurse call" system. such a system provides a means of signal communication between a patient and a nurse located at a central station. In addition, such a system usually provides two-way audio communication between the nurse and the patient. While these systems somewhat improve the communication between a nurse and her patients, they are not entirely satisfactory for a variety of reasons.

Generally speaking, "nurse call" systems do not include different levels of urgency. Hence, the nurse receiving a call does not know whether a call is an emergency call or a non-emergency call. Thus, she must immediately communicate with the patient to determine the nature of the call. If she receives several different calls at one time, she is in a quandary and may miss an emergency call while checking out non-emergency calls.

Nurse call systems are also inadequate because they do not allow a patient to visually view the nurse while orally communicating with her. While oral communications are adequate in some situations, in other situations, it is desirable that the nurse be able to demonstrate visually to the patient one or more of her instructions. If she has no visual communication with the patient, she must walk to the patient's room to provide the necessary visual information.

Another area wherein "nurse call" systems are inadequate relates to their inability to carry information from sensors attached to the patient to either the nurse or to remote recording and analyzing equipment. Hence, localized analyzing and recording equipment must be available near each patient or, as has been suggested in some cases, provision must be made to transmit sensed information from the patient to a remote recording and analyzing device.

With respect to wires, hospital walls contain literally hundreds of wires. Power wires and RF video wires for TV sets located in patient rooms, wires for the nurse call system referred to above, telemetry wires and wires for communication between patients and the nurses stations are all contained in hospital walls. It will be appreciated that it would be desirable to eliminate as many of these wires as possible and utilize only a minimum number of wires to carry a plurality of information signals.

While some attempts have been made to reduce the number of wires in hospital walls for communication and other purposes they have not been entirely successful. Examples of prior art systems proposing solutions to this and other hospital communication problems are described in U.S. Pat. Nos. 3,423,521, 3,517,120 and 3,534,161. While the systems described in these patents appear to improve hospital communications over a simple nurse call system, they still have disadvantages. For example, U.S. Pat. No. 3,517,120 utilizes a complicated oscillator arrangement to notify the nurse at the nurses station that communication is desired. In addition, at the nurses station, there is a means for sensing oscillations at predetermined frequencies to control indicating lights. Such an arrangement is undesirable because oscillators must be tuned and maintained at predetermined frequencies. In addition, detectors must be maintained so that they will detect predetermined frequencies. All these requirements lead to a relatively complicated nurse call arrangement. The other patents (U.S. Pat. Nos. 3,423,521 and 3,534,161) noted above disclose relatively complicated systems for determining exactly which one of a plurality of patients is attempting to communicate with the nurses station. Because of their complexity, such arrangements are expensive to manufacture and install. In addition, because they include a large number of components, they are less reliable than a system using a smaller number of components.

Therefore, it is an object of this invention to provide a new and improved communication system.

It is also an object of this invention to provide a hospital communication system that includes a provision for a patient calling a nurse at a nurses station on either an emergency or a non-emergency basis.

It is another object of this invention to provide a communication system suitable for allowing a patient to view a nurse at a nurses station while the patient is communicating with the nurse.

It is a further object of this invention to provide a new and improved hospital communication system that includes a single coaxial connector for carrying a variety of signals between a patient and a nurse located at a nurses station.

It is a still further object of this invention to provide a new and improved hospital communication system that utilizes the TV receiver which is normally located in a patient's room as a means of visually communicating between a patient and a nurse regardless of whether or not the TV set is energized when communication commences.

It is yet another object of this invention to provide an uncomplicated system for signaling between a patient and a nurse located at a nurses station.

It is a still further object of this invention to provide a nurse call system combined with a communication system that utilizes DC as the basis for the nurse call system.

SUMMARY OF THE INVENTION

In accordance with principles of this invention a communication system that uses a separate single coaxial cable to link a nurses station to each of a plurality of patient rooms or beds is described. DC is used as the basis for signaling between the rooms or beds and the station to "call" a nurse either on an emergency or on a non-emergency basis.

In accordance with further principles of this invention the coaxial cable between each room or bed and the nurses station also carries AC power to power TV receivers located in the patient's room. Further, the same coaxial cable carries RF video (and audio) signals to the receivers.

In accordance with other principles of this invention, the coaxial cables between the beds or rooms and the nurses station also carry communication signals between the patients and the nurses station. If desired, communication can be visual, as well as oral. Further, the coaxial cables can be adapted to carry telemetry from patient sensors to the nurses station and then to remote recording or analyzing devices.

In accordance with still further principles of this invention, the inventive system is adapted to automatically cause the patient to view the nurse on "his" TV receiver, regardless of whether the TV receiver was on or off at the time communication commences.

It will be appreciated from the foregoing brief summary of the invention that a new and improved communication system is provided by the invention. Because the communication system utilizes a single coaxial cable to carry a plurality of different types of information signals, the bundles of wires previously utilized in hospital communication, telemetry and other systems can be eliminated. In addition, because the system uses DC as the basis for nurse call signaling, complicated oscillators or other devices previously used to identify the location of a particular communication signal are not required. Thus, both the complexity and the expense of the system is greatly reduced. Yet, the system is adaptable to provide a wide variety of information either to the nurse or other remote locations. Further, the system makes use of normally available equipment, such as TV receivers which are usually located in patient's rooms.

BRIEF DESCRIPTION OF THE DRAWINGS

The foregoing objects and many of the attendant advantages of this invention will become more readily appreciated as the same becomes understood by reference to the following detail description when taken in conjunction with the accompanying drawings wherein:

FIG. 1 is a block diagram of a preferred embodiment of the invention;

FIG. 2 is a schematic diagram of a power supply suitable for use in the preferred embodiment of the invention;

FIG. 5 is a schematic diagram of a flasher unit suitable for use in the preferred embodiment of the invention; and, FIG. 6 is a schematic diagram of a nurse communication unit suitable for use in the preferred embodiment of the invention.

DESCRIPTION OF THE PREFERRED EMBODIMENT

Figure 3:
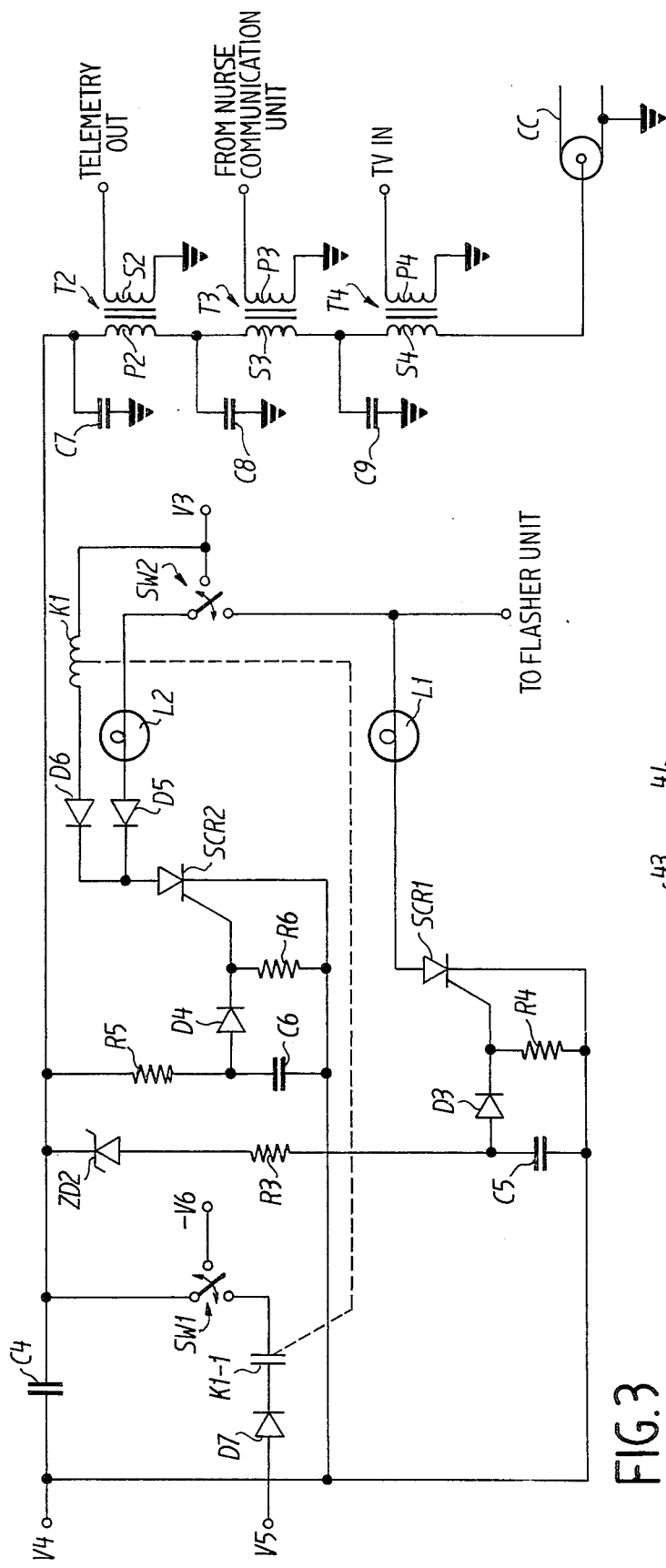
FIG. 3 is a schematic diagram of a nurse control unit suitable for use in the preferred embodiment of the invention.

FIG. 1 is a block diagram that illustrates a preferred embodiment of the invention and comprises a power supply 11; a nurse control unit 13; a flasher unit 15; a nurse communication unit 17; and four patient units 19. The power supply 11 receives conventional 120 V 60 cycle AC power. The power supply provides power for the nurse control unit 13, the flasher unit 15 and the nurse communication unit 17. In addition, the nurse control unit receives a TV signal from an antenna or other suitable source via an input terminal 21. And, the nurse control unit includes a telemetry output terminal 23 for transmitting telemetry to a suitable recording or analyzing device.

The flasher unit 15 and the nurse communication unit 17 are both connected to the nurse control unit 13. In addition, the nurse control unit is connected to the four patient units 19 via four separate coaxial cables 25. It will be appreciated that while only four patient units 19 are illustrated in FIG. 1, more or less than this number can be utilized in an actual embodiment of this invention.

The power supply 11 as stated above provides power to the nurse control unit, the flasher unit and the nurse communication unit. The nurse control unit relays power, as will be better understood from the following description, to TV sets forming part of the patient units 19. In addition, the nurse control unit includes means for passing visual and oral communication signals from the nurse communication unit 17 to the patient units 19. Further, the nurse control unit is under the control of the flasher unit in the sense that when desired the flasher unit can cause the nurse control unit to generate a flashing signal, rather than a constant signal to alert the nurse to the reception of a call.

FIG. 2 is a schematic diagram of a power supply suitable for use in the embodiment of the invention illustrated in FIG. 1. The power supply comprises a power transformer designated T1 having a primary winding designated P1 that receives 120 V 60 cycle AC power. T1 is a stepdown transformer and also includes a plural tap secondary winding designated S1. The tap at one end of S1 is grounded. The remaining taps moving from the grounded end of S1 to the other end in order of voltage levels are designated V1, V2, V3, V4, and V5. By way of explanation in this description, V designates a voltage source or voltage source connection. A V without a prefix (either + or −) designates an AC voltage. A V with a prefix (either + or −) designates a DC voltage of either positive or negative polarity, as the case may be.

The power supply illustrated in FIG. 2 also comprises two diodes designated D1 and D2; a zener diode designated ZD1; three capacitors designated C1, C2 and C3; and, two resistors designated R1 and R2. The anode of D1 is connected to V3 and the cathode of D1 is connected through C1 to ground. The junction between D1 and C1 is connected through R1 to a terminal designated +V7. The cathode ZD1 is connected to +V7 and the anode of ZD1 is connected to ground. The cathode of D2 is connected to V2. The anode of D2 is connected through R2 to a terminal designated −V6. Connected in parallel with R2 are series connected C2 and C3. The junction between C2 and C3 is connected to V4. It will be appreciated from this description of the power supply circuit illustrated in FIG. 2 that the AC power between V2 and V4 is rectified by D2 and filtered by C2, C3 and R2 to provide a negative DC voltage at the terminal designated —V6. It will also be appreciated that D1 rectifies the voltage between V3 and ground. The latter rectified voltage is filtered by C1 and R1 to provide a positive DC voltage at +V7. This latter voltage is regulated by ZD1 to a desired level.

FIG. 3 is a schematic diagram illustrating a nurse control unit suitable for use in the preferred embodiment of the invention. The nurse control unit illustrated in FIG. 3 comprises: five diodes designated D3, D4, D5, D6, and D7; a zener diode designated ZD2; two silicon controlled recitifiers designated SCR1 and SCR2; six capacitors designated C4, C5, C6, C7, C8 and C9; two single pole double throw switches designated SW1 and SW2; four resistors designated R3, R4, R5 and R6; a relay having a coil designated K1 and a set of normally open contacts designated K1-1; and, three signal transformers designated T2, T3 and T4 having primary winding designated P2, P3, and P4 and secondary windings designated S2, S3 and S4, respectively. Also illustrated in FIG. 3 are a pair of indicator lights L1 and L2. Preferably, L1 is a red indicator light and L2 is a white indicator light.

Terminal V4 of the power transformer (FIG. 2) is connected through C4 to one end of P2. The other end of P2 is connected to one end of S3 and the other end of S3 is connected to one end of S4. The other end of S4 is connected by a suitable connector (not shown) to the signal wire of a coaxial cable designated CC. The shield of the coaxial cable is connected to ground. The junction between C4 and P2 is connected through C7 to ground. The junction between P2 and S3 is connected through C8 to ground and the junction between S3 and S4 is connected through C9 to ground.

One end of S2 is connected to ground and the other end is connected to a telemetry output terminal. One end of P3 is connected to ground and the other end is connected to a terminal designated "from nurse communication unit." This means that the latter terminal is connected to the nurse communication unit illustrated in FIG. 5 and hereinafter described. One end of P4 is connected to ground and the other end is connected to a TV input terminal adapted to be connected to a TV antenna or other source of conventional TV signals.

The anode of D7 is connected to terminal V5 of the power transformer (FIG. 2) and the cathode of D7 is connected through K1-1 to one of the switch terminals of SW1. The other switch terminal SW1 is connected to —V6 (FIG. 2). The common terminal of SW1 (the one connected to the movable element) is connected to the end of C4 remote from V4.

The end of C4 remote from V4 is also connected to the cathode of ZD2. The anode of ZD2 is connected through R3 in series with C5 to V4. The junction between R3 and C5 is connected to the anode of D3. The cathode of D3 is connected to the gate of SCR1 and through R4 to V4. The cathode of SCR1 is also connected to V4. The anode of SCR1 is connected through L1 to a terminal designated "to flasher unit." The latter terminal is connected to the flasher unit illustrated in FIG. 5 hereinafter described. In addition, this terminal is connected to one of the switch terminals of SW2. The other switch terminal of SW2 is connected to V3 (FIG. 2), and to one end of K1. The other end of K1 is connected to the anode of D6. The cathode of D6 is connected to the anode of SCR2 and to the cathode of D5. The anode of D5 is connected through L2 to the common terminal of SW2. The cathode of SCR2 is connected to V4. The gate of SCR2 is connected through R6 to V4 and to the cathode of D4. The anode of D4 is connected through R5 to the side of C4 remote from V4, and through C6 to V4.

Figure 4:
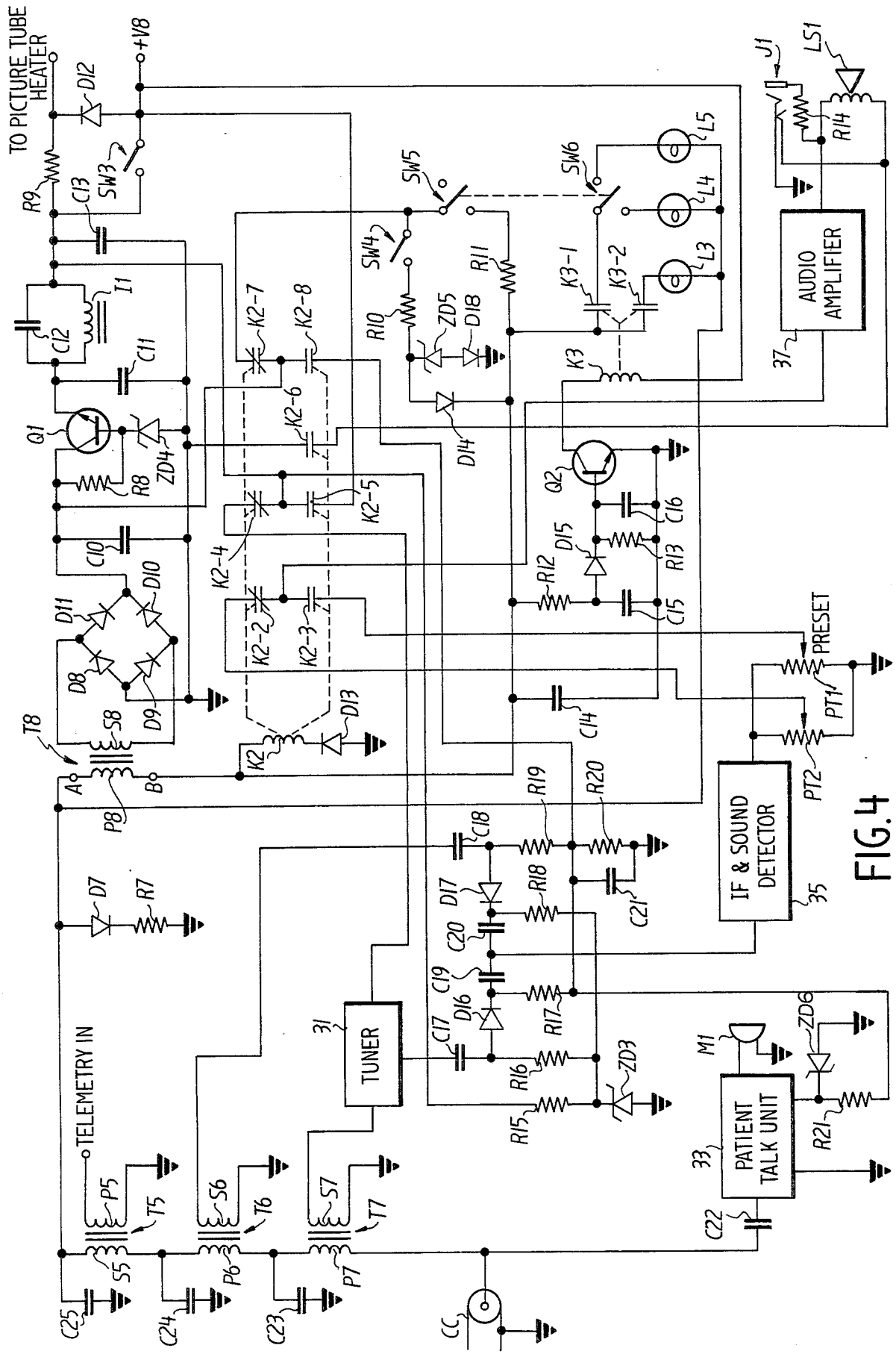
FIG. 4 is a schematic diagram of a single patient unit suitable for use in the preferred embodiment of the invention.

FIG. 4 is a schematic diagram illustrating a patient unit. The patient unit illustrated in FIG. 4 comprises four zener diodes designated ZD3, ZD4, ZD5 and ZD6; 12 diodes designated D7 through D18; 15 resistors designated R7 through R21; two potentiometers designated PT1 and PT2; 16 capacitors designated C10 through C25; an earphone jack designated J1; an inductor designated I1; two NPN transistors designated Q1 and Q2; a loudspeaker designated LS1; four switches designated SW3, SW4, SW5 and SW6; and, a microphone designated M1. Also illustrated in FIG. 4 is a first relay designated K2 having three sets of normally closed contacts designated K2-2, K2-4, and K2-7 and four normally open contacts designated K2-3, K2-5, K2-6 and K2-8; and, a second relay designated K3 having two sets of normally open contacts designated K3-1 and K3-2. Further illustrated in FIG. 4 are three signal transformers designated T5, T6, T7 having primary windings designated P5, P6 and P7 and secondary windings designated S5, S6, and S7, respectively. In addition, illustrated in FIG. 4 is a power transformer designated T8 having a primary winding designated P8 and a secondary winding designated S8. Finally, three indicator lights designated L3, L4 and L5 are illustrated in FIG. 4; L4 is preferably red.

The shield of the coaxial cable designated CC is connected to ground and the signal wire of CC is connected to one end of P7. The other end of P7 is connected through P6 to one end of S5. The other end of S5 is connected to one end of P8. This end of P8 for ease of description purposes is herein designated point A. The junction between P7 and P6 is connected through C23 to ground. The junction between P6 and S5 is connected through C24 to ground and the junction between S5 and P8 is connected through C25 to ground. The junction between S5 and P8 is also connected to the anode of D7. The cathode of D7 is connected through R7 to ground.

D8, D9, D10 and D11 comprise a full-wave rectifying bridge connected to S8. More specifically, one end of S8 is connected to the cathode of D8 and to the anode of D11, and the other end of S8 is connected to the cathode of D9 and to the anode of D10. The anode of D9 and the anode of D8 are connected to ground. The cathode of D10 and the cathode of D11 are connected through C10 to ground. The ungrounded end of C10 is also connected to the collector of Q1. R8 is connected between the collector and the base of Q1. The emitter of Q1 is connected through C11 to ground. The base of Q1 is connected to the cathode of ZD4, and the anode of ZD4 is connected to ground. The emitter of Q1 is also connected to one end of I1 and one end of C12. The other ends of I1 and C12 are connected together and through C13 to ground. The ungrounded end of C13 is connected through R9 to a terminal designated "to picture tube heater." This latter terminal is connected to the picture tube of the TV set located in the patient's room and is also connected to the cathode of D12. The anode of D12 is connected to a terminal designated +V8.

SW3 is a single pole single throw switch. The anode of D12 is also connected to the movable element of SW3. The switch terminal of SW3 is connected to the junction between R9 and C13.

It will be appreciated from the foregoing description that the diode bridge rectifies the AC signal across S8. This signal is smoothed by C10. In addition, Q1 and ZD4 comprise a series voltage regulator circuit that controls the level of the rectified voltage. In this manner, the power for the patient's TV receiver is carried from the nurses station to the TV receiver via the coaxial cable.

The other end of P8 is designated point B for ease of description purposes and is connected through K2 to the cathode of D13. The anode of D13 is connected to ground. Point B also connected to the cathode of D14. The anode of D14 is connected to the cathode of ZD5. The anode of ZD5 is connected through diode D18 to ground. The junction between D14 and ZD5 is connected to one end of R10. SW4 is a momentary contact (push button) single pole single throw switch. The switch terminal of SW4 is connected to the other end of R10.

SW5 is ganged with SW6 to provide a double pole double throw switch. However, one of these switch terminals of SW5 is unconnected. The common terminal of SW5 is connected to the movable contact terminal of SW4. In addition, the other switch terminal of SW5 is connected through R11 to the cathode of D14 (point B).

Point B is further connected through C14 to ground and through R12 in series with C15 to ground. The junction between R12 and C15 is connected to the anode of D15. The cathode of D15 is connected through R13 to ground, and through C16 to ground. The anode of D15 is also connected to the base of Q2. The emitter of Q2 is connected to ground, and the collector of Q2 is connected through K3 to +V8. One end of K3-1 is connected to point B. The other end of K3-1 is connected to the common terminal of SW6. One of the switch terminals of SW6 is connected through L5 to point A. The other switch terminal of SW6 is connected through L4 to point A. One end of K3-2 is connected to point B and the other end of K3-2 is connected through L3 to point A.

Returning now to the signal transformers, one end of S6 is connected to ground. The other end of S6 is connected through C18 in series with R19 and R20, in that order, to ground. The junction between C18 and R19 is connected to the anode of D17. The cathode of D17 is connected through R18 to the cathode of ZD3. The anode of ZD3 is connected to ground. C21 is connected in parallel with R20. The cathode of D17 is connected through C20 and C19, connected in series, to the cathode of D16. The anode of D16 is connected through R16 to the cathode of ZD3. The anode of D16 is also connected through C17 to the signal output of a tuner 31. The tuner 31 is the tuner of the patient's TV receiver.

The signal input to the tuner 31 is connected to one end of S7. The other end of S7 is connected to ground. A control input to the tuner 31 is connected to one end of K2-4. The other end of K2-4 is connected to the junction between C13 and R9. The other end of K2-4 is also connected to one side of K2-5 and through R15 to the cathode of ZD3. The other end of K2-5 is connected to +V8.

The junction between D16 and C19 is connected through R17 to one end of K2-8. The other end of K2-8 is connected to the collector of Q1 and to one end of K2-7. The other end of K2-7 is connected to the junction between SW4 and SW5. The same end of K2-8 that is connected to R17 is also connected to the point where R19 and R20 join. Further, that same point is connected through R21 to the control input of a patient talk unit 33.

The patient talk unit 33 is basically a transmitter connected to M1 to amplify the input from M1. The output from the patient talk unit is connected through C22 to the signal wire of CC. In addition, the control input of the patient talk unit 33 is connected to the cathode of ZD6. The anode of ZD6 is connected to ground.

The junction between C19 and C20 is connected to the signal input of an IF and sound detector 35 which also forms part of the patient's TV receiver. The output from the IF and sound detector is connected through PT2 to ground, and through PT1 to ground. The movable contact terminal of PT2 is connected to one end of K2-2. The movable contact terminal of PT1 is connected to one end of K2-3. The other ends of K2-2 and K2-3 are connected together and to the input of the audio amplifier 37 of the patient's TV receiver.

The output of the audio amplifier 37 is connected through R14 to the signal terminal of J1 and through the coil of LS1 to one end of K2-6. The other end of K2-6 is connected to ground. In addition, J1 includes an internal switch connection to the end of LS1 connected to K2-6.

Finally, one end of P5 is connected to ground and the other end is connected to an input terminal designated "telemetry in." This latter terminal receives telemetry from sensors connected to the patient (not shown).

FIG. 5 is a schematic diagram of a flasher unit suitable for use in the embodiment of the invention illustrated in FIG. 1. The flasher unit illustrated in FIG. 5 comprises a diode designated D19; a unijunction transistor designated UJT; an NPN transistor designated Q3; a silicon controlled recitifier designated SCR3; two capacitors designated C26 and C27; and, seven resistors designated R22 through R28. V2 (FIG. 2) is connected to the anode of D19 and to the anode of SCR3. The cathode of D19 is connected through C26 to V4 (FIG. 2). Connected in parallel with C26 are R22 and C27 connected in series. The junction between R22 and C27 is connected to the emitter of UJT. B1 of UJT is connected through R24 to V4 and B2 of UJT is connected through R23 to the junction between the cathode of D19 and C26. The junction between R22 and C27 is also connected through R25 to V4, and to the base of Q3. The collector of Q3 is connected to the junction between D19 and C26. The emitter of Q3 is connected through R26 to the gate of SCR3. The cathode of SCR3 is connected through R27 and R28 (connected in parallel) to V4. The cathode of SCR3 is also connected to a terminal designated "to nurse control unit." This terminal is connected to the terminal designated "to flasher unit" in FIG. 3.

Basically, FIG. 5 illustrates a UJT oscillator circuit wherein the oscillations of the circuit are utilized to control the on and off switching of SCR3. This on and off switching is utilized, as will be better understood from the following description, to control the flashing of L1.

Figure 6:
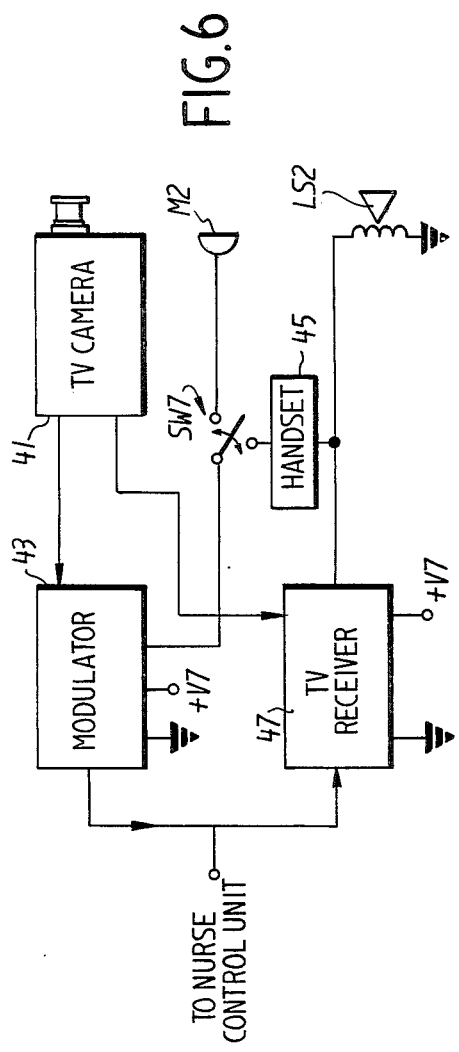

FIG. 6 illustrates, in block form, a nurse communication unit suitable for use in the embodiment of the invention illustrated in FIG. 1. The nurse communication unit comprises a TV camera 41, a modulator 43, a hand set 45, and a TV receiver 47. In addition, FIG. 6 illustrates a microphone designated M2, a loudspeaker designated LS2 and a switch designated SW7. SW7 is a single pole double throw switch.

The TV camera 41 is pointed at a nurse sitting in a suitable position at the nurse control station. Thus, the TV camera is adapted to generate a picture of the nurse. The output from the TV camera is connected to the TV receiver 47. The TV receiver is located at the nurse control station so that the nurse can see that her image is being transmitted. The TV camera also applies a picture signal to the modulator 43. The modulator 43 modulates this signal and applies it to an output terminal designated "to nurse control unit." This output terminal is connected to the terminal designated "from nurse communication unit" in FIG. 3. The modulator is connected to the +V7 voltage source as is the TV receiver 47. In addition, the modulator and TV receiver are suitably grounded. The TV receiver, if desired, also receives a picture signal from a camera (not shown) viewing the patient. Such an arrangement, while not illustrated and described in detail herein, is an obvious modification of the instant invention.

In any event, SW7 includes two switch terminals and a common terminal. The common terminal is connected to the modulator 43. One terminal of the switch terminal is connected to M2 and the other terminal is connected to the handset 45. The handset 45 is also connected to one end of the coil of LS2. The same end of the coil of LS2 is also connected to the TV receiver 47. The other end of LS2 is grounded. In this way, either M2 in combination with LS2 can be utilized for oral communications or the handset 45 can be utilized for oral communications. In operation, the picture signal from the TV camera 41 is viewed on the TV receiver 47 and is modulated. The modulated signal is transmitted through CC to the patient's receiver for viewing as hereinafter described. In addition, the audio input from M2 or the handset is modulated and transmitted via CC.

Turning now to a more complete description of the operation of the invention, as previously indicated, the V4 voltage level is adequate to meet all the requirements of a conventional hospital TV receiver 24 volts RMS, for example. The V4 voltage is applied to the coaxial cable CC via the nurse control unit 13. With regard to the transmission of power it is pointed out that while T1 acts as a heavy duty stepdown transformer which supplies voltage to the TV receiver of all of the patient units, T8 merely acts as an isolation voltage adjusting transformer which serves only one such receiver. C4 and C14 are non-polarized capacitors that have negligible reactance at 60 cycles. If it is assumed that load represents about 12 watts, the load current through CC is about ½ ampere. Under these conditions the voltage drop across both capacitors will be only about 1 ⅓ volts — assuming their (C4 and C14) size to be 2,000 Mfd. Thus, the ripple voltage across these capacitors will only be about ⅔ volt, an acceptable level. For these conditions DC signaling can be readily accomplished along the same line, i.e., CC. Preferably signaling is accomplished using +6 volts DC for one type of a nurse call situation (i.e., a nonemergency call) and +12 volts DC for a second type of a nurse call situation (i.e., an emergency call). The following description describes how the invention accomplishes this result using these voltage levels. However, it is to be understood that other voltage levels could be used.

SW4 is, preferably, a spring loaded momentary contact switch and forms the nurse call switch for a "normal" call. When SW4 is momentarily closed a voltage is applied to CC via K2-7, SW4, R10, D14, P8, S5 P6 and P7. Assuming that ZD5 is choosen to limit this voltage to +6 volts, 6 volts is applied to CC. K2 at this point remains in its non-energized state because D13 is back biased by the +6 volts. The +6 volts on CC is applied through R5 (of the nurse control unit — FIG. 3) to the anode of D4 and triggers SCR2 on. Assuming that the common terminal of SW2 is connected to V3 at this time L2 is lit to inform the nurse of a normal call. If SW2 is in its other position (i.e., connected to flasher unit when SW4 is closed) L2 will flash on and off at the frequency of oscillation of the UJT oscillator circuit described above and illustrated in FIG. 5. Thus, by controlling the position of SW2 the nurse controls whether a normal cell creates a constant light or a flashing light.

In addition to energizing L2, K1 is also energized when SW4 is closed to place +6 volts on CC. When K1 is energized, contacts K1-1 close and a holding voltage of approximately +6 volts is applied to the gate of SCR2 via D4 assuming SW1 is completing the circuit therebetween as it should be at this point, More specifically, the voltage difference between V4 and V5 is rectified by D7. This rectified DC voltage is about +6 volts and applied via a closed SW1 through D4 to the gate of SCR2 so that SCR2 remains energized. It would be appreciated that SCR2 would end conduction on the back bias cycle from V3 if this "holding" voltage were not provided. The +6 volts on CC in addition to keeping L2 lit also causes the patient's light (L4) and one of the corridor lights (L5) to be lit, as hereinafter described.

Turning now to a description of what occurs when an emergency call situation occurs, when an emergency occurs the patient changes the position of SW5 rather than closes SW4. SW5 is normally open, when it changes position it applies a +12 rather than a +6 volt DC voltage to CC. This voltage is applied to CC via R11, P8, S5, P6 and P7. Since ZD5 is now bypassed it has no effect. When +12 volts is applied to CC, not only is L2 energized but the breakdown voltage of ZD2 is also overcome. Since ZD2 is now triggered, a voltage is applied to the gate of SCR1 via D3 and L1 is also lit. L1 is constantly flashing on and off since it is connected directly to the flasher unit. Since L1 is preferably a colored light, such as red, the nurse monitoring system is automatically notified of the existence of an emergency. Knowning which light of several (there is one related to each patient unit) is lit immediately informs her of which patient needs her attention in a hurry.

It is desirable that a light be lit adjacent to the patient, either in a patient control handset (which houses SW4 or SW5) or adjacent to his bed to indicate that a signal of one type or another (normal or emergency) has been generated and transmitted to the nurses station. Such a light is provided by the invention. More specifically, when either +6 or +12 volts is applied to CC, the same voltage is applied to Q2 via D15. Either of these voltages causes Q2 to energize K3. When K3 is energized, K3-2 closes and a current flows through L3. Assuming L3 is located at a suitable position near the patient it provides the desired patient signal.

It is also desirable that corridor lights outside of a patient's room be lit to indicate that either a normal or an emergency call has been sent to the nurses station.

Such lights are useful to alert "roving" nurses of the patients need for attention. Such lights are also provided by the invention because K3-1 closes at the same time that K3-2 closes. Depending upon the position of SW6 when K3 is energized to close K3-1 and K3-2, either L4 or L5 is energized. If SW4 is closed, 6 volts is applied to CC and a "normal" call is produced and L5 is lit. Since this is a "normal" call, L5 should be a white light. On the other hand, if SW5 and SW6 are positioned such that +12 volts is being applied to CC, then L4 is lit. Since this is the emergency call situation, L4 should be red light. It will be appreciated that SW5/SW6 is a gang switch which must be manually reset.

It should be noted that R10 and R11 are provided to limit the current in the system when the call is answered in the manner as will now be described and permit the nurses station to apply negative voltage to the line. In order to answer a call the nurse switches SW1 to its other position i.e. from connection to K1-1 to connection to −V6. This action opens the holding circuit and L1, L2, L3, L4 and L5 go out. More specifically, even if the patient maintains either SW4 or SW5 closed, the line voltage drops below zero because the value of −V6 is above +6 to +12 volts, such as −15 volts, for example. Because this voltage is negative, it overcomes the positive voltage caused by SW4 or SW5 being closed. Since the voltage on the gates of SCR1 and SCR2 is now negative L1 and L2 go out on the back bias cycle of V3. In addition K1 is de-energized and K1-1 opens. Further the base of Q2 is reverse biased and thus K3 is de-energized, and K3-1 and K3-2 open.

In addition to de-energizing the lights, switching SW1 to its −V6 status also causes current to flow through K2. Energization of K2 causes the normal states of K2-2 through K2-8 to reverse. Because K2-2 opens and K2-3 closes, the output of the IF and sound detector circuit 35 is switched from a patient control condition wherein PT2 controlled the audio level of LS1 to a preset condition wherein PT1 controls the audio level of LS1. In other words, PT1 is preset to a predetermined volume setting which cannot be changed by the patient. On the other hand, PT2 is a patient controlled potentiometer which allows the patient to control the volume of LS1 (or the earphone connected to J1). When K2 is energized, PT2 is taken out of the audio circuit and PT1 is put into the audio circuit.

When K2 is energized, K2-4 is opened and K2-5 is closed. Closure of K2-5 bypasses the on-off switch (SW3) of the TV receiver. Thus, the TV receiver is automatically energized regardless of whether or not it was energized at the time SW1 changed position. Opening K2-4 disables the tuner 31 so that it no longer applies to the picture tube of the TV receiver the signal across S7. As will be hereinafter described this is a conventional TV input signal. The tuner selects the desired channel in a conventional manner.

Energization of K2 causes K2-6 to close. Closure of K2-6 applies the output from the audio amplifier 37 to LS1 regardless of whether or not J1 (the earphone jack) was being used by the patient. In addition, the position changing of K2-7 and K2-8 causes the diode switch comprising the circuitry in and around and including D16 and D17 to switch its output. Previously, the output from the tuner of the TV set was being applied to the IF and sound detector 35 via D16. However, when K2-7 opens and K2-8 closes, the output from signal transformer T6 is applied via D17 to IF and sound detector 35. Thus, the TV receiver is automatically "tuned" to the frequency of the signal generated by the modulator 43 in the nurse communication unit. Consequently, the system has now been automatically conditioned so that the nurse can orally communicate with the patient via the loudspeaker of the TV receiver. In addition, the patient, via the patient talk unit 33 can now communicate with the nurse. He could not do this previously because that unit was disabled via K2-8 being open. In addition, the Tv picture of the nurse taken by TV camera 41 is automatically applied to the picture of the TV set regardless of whether or not the TV set was previously energized.

At the end of communication, restoration of SW1 to its previous state leaves the line in an essentially zero signal voltage state whereby the indicating lights are out and the system is ready for the next call, either normal or emergency.

Turning now to a more general discussion of the application of a TV signal to the patient's TV receiver, under normal circumstances the TV signal is received at the TV input illustrated in FIG. 3. It is coupled via T4 to the signal line of CC. Via CC the signal is applied to T7. This signal is thus applied to tuner 31. Tuner 31 is tuned to the desired channel in a conventional manner and the signal from the desired channel is applied via D16 to the IF and sound detector and thence to other circuits for picture display and sound emission is a conventional manner. When the system is seized in the manner previously described, portions of the TV receiver circuitry are changed so that the nurse can be viewed on the screen of the picture tube and communicate with the patient.

In a similar manner, telemetry from sensors attached to the patient are applied to the telemetry terminal illustrated in FIG. 4. This terminal is coupled via T5 to CC. On the othe end of CC it is detected by T2 in combination with C7 and applied to an output terminal. The output terminal is connected to suitable recording and analyzing devices. Alternatively, the output terminal can be connected to a further coaxial conductor for transmission to a remote location.

With respect to frequency ranges, and only by way of example, 50 – 250 MHz is an adequate bandwidth for transmitting video signals. Thus, if C9 and S4 and P7 and C23 are selected to be series resonant about 50 MHz signals in the 50 – 250 MHz range can be carried by CC, as will be understood by those skilled in the art. If S3 and C8, and P6 and C24 are adapted to resonate at about 20 MHz then T3 can feed energy into the communications line between 20 MHz and 50 MHz. This bandwidth is adequate to transmit the nurse's TV picture to the patient's receiver and handle communication between the patient and the nurse. Similarly, if P2 and C7, and S5 and C25 are chosen to resonate at 2 MHz then 2 to 20 MHz is available for telemetry purposes. This makes approximately 360 channels of wide band telemetry available. Thus, telemetry, TV communication and TV reception are all available on one coaxial cable, in addition to DC signaling. Further, other frequency bands are available if desired. All that is needed are suitable filtering signal transformers.

It will be appreciated from the foregoing description of a preferred embodiment of the invention a new and improved communication system suitable for use in hospitals and other locations is provided. The communication system utilizes Dc to provide a signalling.

Thus, complicated oscillators and location indicating devices are not necessary. In addition, the invention uses a single coaxial cable for signaling purposes as well as for communication purposes. Moreover, the same conductor is utilized for telemetry transmission and for conventional TV reception. Hence, the invention provides an overall uncomplicated system with wide flexibility for communication and other signaling purposes. Yet only a single cable is used.

It will be appreciated by those skilled in the art and others that while the preferred use of the invention is in a hospital, it can be utilized in other environments where similar communication problems exist. It will also be appreciated that while a preferred embodiment of the invention has been illustrated and described, various changes can be made therein without departing from the spirit and scope of the invention. For example, the various lights could be replaced by audio indicators, if desired. In addition, the ordinary call-emergency call circuitry can be modified, as will be apparent to one skilled in the art, to provide a third signal, such as a fire or smoke signal which could operate another light, which might be yellow. This could be accomplished, for example, by activation of a heat sensitive bimetallic switch which would generate a +18V signal which would trigger a zener diode which breaks down at a voltage greater than +12V and is connected to circuitry similar to that associated with ZD2. Hence, the invention can be practiced otherwise than as specifically described herein.

The invention has been described in detail with particular reference to a preferred embodiment thereof, but it will be understood that variations and modifications can be effected within the spirit and scope of the invention.

I claim:

1. A communication system suitable for use in a hospital and the like to provide communication between patients and a central nurse station, said communication system comprising:
    1. a nurse unit including:
        a. a first indicator means suitable for activation by a patient generated DC signal of a first magnitude to indicate a request for assistance on a non-emergency basis;
        b. a second indicator means suitable for activation by a patient generated DC signal of a second magnitude to indicate a request for assistance on an emergency basis;
        c. a power supply means suitable for powering the nurse unit and suitable for supplying power to at least one patient unit; and,
    2. at least one patient unit including:
        a. a patient controllable first DC signal means for generating a DC signal of a first magnitude for activating said first indicator means of said nurse unit;
        b. a patient controllable second DC signal means for generating a DC signal of a second magnitude for activating said second indicator means of said nurse unit; said first and second magnitudes being different; and,
        c. patient communication means suitable for transmitting audio communication signals and suitable for receiving audio communication signals; and
    3. a single coaxial cable connecting said nurse unit to said at least one patient unit, said single coaxial cable adapted to carry: power from said nurse unit to said at least one patient unit; DC signals from said patient unit to said nurse unit for activation of said first and sdcond indicator means; and, audio communication signals between said nurse unit and said at least one patient unit.

2. A communication system as claimed in claim 1 wherein said patient unit includes an indicator light, said indicator light being lit when said patient unit generates one of said patient controllable first or second DC signals.

3. A communication system as claimed in claim 1 including as part of said patient unit first and second corridor indicator means adapted to be located in the hall adjacent to the room housing said patient unit, said first corridor indicator means being active when said first indicator means of said nurse unit is active and said second corridor indicator means being active when said second indicator means of said nurse unit is activated.

4. A communication system as claimed in claim 1 including means for transmitting telemetry signals from said patient unit to said nurse unit along said coaxial cables.

5. A communication system as claimed in claim 1 including as part of said patient unit first and second corridor indicator lights adapted to be located in the hall adjacent to the room housing said patient unit, said first corridor indicator light being lit when said first indicator means of said nurse unit is activated and said second corridor indicator light being lit when said second indicator means of said nurse unit is activated.

6. A communication system as claimed in claim 1 wherein said nurse unit includes means for selectively energizing said first and second indicator means in accordance with whether said patient unit generates a first or a second DC signal.

7. A communication system as claimed in claim 1 wherein:
    said nurse unit includes a television transmitter including a TV camera mounted so as to view a nurse; and,
    said patient unit includes a TV receiver, said communication system including means for automatically transmitting a video picture of said nurse to said patient TV receiver when said nurse is in audio communication with a patient whereby said patient receives visual as well as audio communication from said nurse unit.

8. A communication system as claimed in claim 7 wherein said nurse unit is adapted to receive commercially generated TV signals and transmit them to said patient TV receiver via said coaxial cable and wherein said patient TV receiver is adapted to normally receive said commerical TV signals, said patient TV receiver being adapted to automatically switch from displaying said commercial TV signals to a view of said nurse when said nurse is in communication with a patient.

9. A communication system as claimed in claim 1 wherein said first and second indicator means are lights and including a flasher unit connected to said lights so as to cause said first and second lights to flash on and off when either of said first and second lights are activated by an appropriate DC signal from said patient unit.

10. A communication system as claimed in claim 9 wherein said nurse unit includes means for selectively energizing said first and second indicator lights in accordance with whether a patient unit generates a first or a second DC signal.

11. A communication system suitable for use in a hospital and the like to provide communication between patients and a central nurse station, said communication system comprising:
  a nurse unit including:
    a first indicator means suitable for activation by a patient generated DC signal to indicate a request for assistance on a non-emergency basis;
    a second indicator means suitable for activation by a patient generated DC signal to indicate a request for assistance on an emergency basis;
    a power supply means suitable for powering the nurse unit and suitable for supplying power to at least one patient unit; and,
  at least one patient unit including:
    a patient controllable first DC signal means for generating a DC signal suitable for activating said first indicator means of said nurse unit;
    a patient controllable second DC signal means for generating a DC signal suitable for activating said second indicator means of said nurse unit; and,
    a patient communication means suitable for transmitting audio communication signals and suitable for receiving audio communication signals; and,
  a single coaxial cable connecting said nurse unit to said at least one patient unit, said signal coaxial cable adapted to carry: power from said nurse unit to said at least one patient unit; DC signals from said patient unit to said nurse unit for activation of said first and second indicator means; and, audio communication signals between said nurse unit and said at least one patient unit,
  said nurse unit including a television transmitter including a TV camera mounted so as to view a nurse;
  said patient unit including a TV receiver, said communication system including means for automatically transmitting a video picture of said nurse to said patient TV receiver when said nurse is in audio communication with a patient whereby said patient receives visual as well as audio communication from said nurse unit;
  said nurse unit being adapted to receive commercially generated TV signals and transmit them to said patient TV receiver via said coaxial cable and wherein said patient TV receiver is adapted to normally receive said commercial TV signals, said patient TV receiver being adapted to automatically switch from displaying said commercial TV signals to a view of said nurse when said nurse is in communication with a patient; and
  said means for automatically switching from a regular or normal TV program to display a nurse's image on the receiver of said patient TV receiver comprising a relay means activated by said nurse unit, said relay means when activated automatically: turning on said patient TV receiver, if said patient TV receiver was not previously on; tuning said patient TV receiver to receive the frequency of the video transmission from the nurse unit; switching the loudspeaker of said patient TV receiver to an active state; and, controlling the volume of the sound emitted from said patient TV receiver.

12. A communication system suitable for use in a hospital and the like to provide communication between patients and a central nurse station, said communication system comprising:
  a nurse unit including:
    a plurality of indicator means suitable for activation by a patient generated DC signal to indicate a request for assistance on a non-emergency basis;
    a plurality of second indicator means suitable for activation by a patient generated DC signal to indicate a request for assistance on an emergency basis;
    a power supply means suitable for powering the nurse unit and suitable for supplying power to at least one patient unit; and
  a plurality of patient units each of which includes:
    a patient controllable first DC signal means for generating a DC signal suitable for activating a related first indicator means of said nurse unit;
    a patient controllable second DC signal means for generating a DC signal suitable for activating a related second indicator means of said nurse unit; and,
    patient communication means suitable for transmitting audio communication signals to and suitable for receiving audio communication signals from said nurse unit;
  a single coaxial cable connecting said nurse unit to each patient unit, said coaxial cables adapted to carry: power from said nurse unit to said patient units; DC signals from said patient units to said nurse unit for activation of said first and second indicator means; and, audio communication signals between said nurse unit and said patient units,
  said nurse unit including a television transmitter including a TV camera mounted so as to view a nurse; and,
  each of said plurality of patient units including a TV receiver, said communication system including means for automatically transmitting a video picture of said nurse to a patient TV receiver when said nurse is in audio communication with a patient whereby said patient receives visual as well as audio communication from said nurse unit;
  said nurse unit being adapted to receive commercially generated TV signals and transmit them to all of said patient TV receivers via said coaxial cables and wherein said patient TV receivers are adapted to normally receive said commercial TV signals, said patient TV receivers being adapted to automatically switch from displaying said commercial TV signals to a view of said nurse when said nurse is in communication with a patient; and,
  said means for automatically switching from a regular or normal TV program to displaying a nurse's image on said patient TV receiver comprising a relay means activated by said nurse unit, said relay means when activated automatically: turning on said patient TV receiver, if said patient TV receiver was not previously turned on; tuning said patient TV receiver to receive the frequency of the video transmission from the nurse unit; switching the loudspeaker of said patient TV receiver to an active state; and, controlling the volume of the sound emitted from said patient TV receiver.

13. A communication system suitable for use in a hospital and the like to provide communication between patients and a central nurse station, said communications system comprising:
- a nurse unit including,
  - a microphone,
  - a video transmitting means having a camera which may be directed toward a nurse at said nurse station, and,
  - a control means;
- a plurality of patient units each including a television receiver having audio reception means and patient controlled volume control means; and,
- a coaxial cable interconnecting said nurse unit with each said patient station for transmitting, video, audio and control signals from said nurse unit to said television receivers,
- said control means disabling the patient controlled volume control means when connecting said microphone means to said audio reception means.

14. A communications system as claimed in claim 13 wherein each said television receiver includes a fixed volume control, and switch means responsive to said control means for connecting said fixed volume control into said audio reception means while disconnecting said patient controlled volume control means.

* * * * *